US008999053B2

(12) United States Patent
Friedel et al.

(10) Patent No.: US 8,999,053 B2
(45) Date of Patent: *Apr. 7, 2015

(54) SOLUTION COMPRISING PROPYL-FUNCTIONAL ALKALI SILICONATES, SILICATES AND METHOD OF PRODUCTION THEREOF

(75) Inventors: Manuel Friedel, Zürich (CH);
Spomenko Ljesic, Rheinfelden (DE);
Christian Waβmer, Hausen (DE);
Susanne Zölitz, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/110,840

(22) PCT Filed: Feb. 27, 2012

(86) PCT No.: PCT/EP2012/053269
§ 371 (c)(1),
(2), (4) Date: Feb. 20, 2014

(87) PCT Pub. No.: WO2012/139804
PCT Pub. Date: Oct. 18, 2012

(65) Prior Publication Data
US 2014/0182487 A1    Jul. 3, 2014

(30) Foreign Application Priority Data
Apr. 11, 2011   (DE) .......... 10 2011 007 142

(51) Int. Cl.
C07F 7/18        (2006.01)
C09K 3/18        (2006.01)
C09D 183/04      (2006.01)
C04B 41/49       (2006.01)
C04B 111/10      (2006.01)

(52) U.S. Cl.
CPC . C09K 3/18 (2013.01); C07F 7/188 (2013.01); C09D 183/04 (2013.01); C04B 41/4972 (2013.01); C04B 2111/1012 (2013.01)

(58) Field of Classification Search
CPC ........ C07F 7/18; C07F 7/1804; C07F 7/1872; C09K 3/18

USPC .......... 106/2, 287.1, 287.13, 287.14, 287.15, 106/806
See application file for complete search history.

(56) References Cited

U.S. PATENT DOCUMENTS

| 3,956,570 | A | * | 5/1976 | Bosch et al. ................. 428/446 |
| 4,252,569 | A | | 2/1981 | Roedel |
| 5,356,716 | A | * | 10/1994 | Patel .......................... 428/423.1 |
| 6,084,116 | A | | 7/2000 | Horn et al. |
| 6,770,327 | B2 | | 8/2004 | Edelmann et al. |
| 6,780,955 | B2 | | 8/2004 | Barfurth et al. |
| 6,841,197 | B2 | | 1/2005 | Standke et al. |
| 7,939,616 | B2 | | 5/2011 | Barfurth et al. |
| 8,147,918 | B2 | | 4/2012 | Standke et al. |
| 8,394,885 | B2 | | 3/2013 | Friedel et al. |
| 8,481,654 | B2 | | 7/2013 | Edelmann et al. |
| 8,679,247 | B2 | | 3/2014 | Friedel et al. |
| 2003/0021904 | A1 | | 1/2003 | Hirsbrunner et al. |
| 2011/0308423 | A1 | | 12/2011 | Friedel et al. |
| 2013/0040058 | A1 | | 2/2013 | Friedel et al. |
| 2013/0085210 | A1 | | 4/2013 | Friedel et al. |
| 2013/0087080 | A1 | | 4/2013 | Friedel et al. |
| 2013/0092052 | A1 | | 4/2013 | Friedel et al. |
| 2013/0284071 | A1 | | 10/2013 | Friedel et al. |

FOREIGN PATENT DOCUMENTS

| GB | 856522 | | 12/1960 |
| JP | 53101022 A | * | 9/1978 |
| WO | 02 083808 | | 10/2002 |
| WO | WO 2012/084401 A1 | | 6/2012 |
| WO | WO 2012/139803 A1 | | 10/2012 |
| WO | WO 2012/139804 A1 | | 10/2012 |
| WO | WO 2013/072185 A1 | | 5/2013 |

OTHER PUBLICATIONS

U.S. Appl. No. 14/358,437, filed May 15, 2014, Ljesic, et al.
International Search Report Issued Apr. 19, 2012 in PCT/EP12/53269 Filed Feb. 27, 2012.
U.S. Appl. No. 14/111,185, filed Oct. 11, 2013, Friedel, et al.

* cited by examiner

Primary Examiner — Anthony J Green
(74) Attorney, Agent, or Firm — Oblon, McClelland, Maier & Neustadt, L.L.P.

(57) ABSTRACT

The invention relates to a solution and to methods for producing the solution comprising propylfunctional alkaline siliconates, silicates and, optionally, the cocondensation products thereof.

10 Claims, 2 Drawing Sheets

SOLUTION COMPRISING PROPYL-FUNCTIONAL ALKALI SILICONATES, SILICATES AND METHOD OF PRODUCTION THEREOF

The invention relates to a solution and methods of production of the solution comprising propyl-functional alkali siliconates, silicates and optionally co-condensation products thereof.

Owing to water absorption by porous mineral building materials, such as concrete, sandstones, lime sandstones, gypsum, ceramics or fired clay products, for example bricks, in the presence of water or moisture, the building materials may be damaged. Repair of building materials damaged in this way is very laborious and expensive. Incorporation of hydrophobizing agents on the surface or in the bulk during production of these building materials, in order to prevent water absorption and consequent damage of the building materials, is known. For some time, siliconates have played an important role as hydrophobizing agents, especially when less alkaline building materials, such as clay products, are to be treated.

EP 0 650 968 discloses a two-stage process for continuous production of alkali alkylsiliconates from alkyltrichlorosilanes via alkyltrialkoxysilanes. U.S. Pat. No. 4,281,147 describes a method of production of aqueous alkali organylsiliconates by reaction of organylalkoxypolysiloxanes with NaOH or KOH. EP 0 015 366 relates to a method of production of alkali chloride-free alkali methylsiliconates by reaction of alkali trichlorosilanes with a base, precipitation of the intermediate by acidification and final dissolution of the washed filter cake in base. DE 32 20 393 describes guanidinium organylsiliconates and -silicates and a method of production from organyltrialkoxysilanes and guanidinium hydroxide. U.S. Pat. No. 4,252,569 discloses a method of production of sodium methylsiliconates by reaction of sodium methyltrichlorosilanes with a methanol/water mixture in a first step, after which the reaction products are put into aqueous sodium hydroxide solution. The main drawback of the method described is the need for phase separation after the first reaction step. WO 02/083808 discloses the hydrophobizing action of mixtures of 20 ml water, a defined amount of 28% potassium methylsiliconate and/or technical sodium silicate (waterglass) with 28% $SiO_2$, which are prepared by mixing and are dried onto sand immediately at 60° C.

Neither a composition comprising propyl-functional alkali siliconates, silicates and co-condensates thereof, nor a technical method for the industrial production of said composition, are known from the prior art. Furthermore, no solution of a propyl-functional siliconate is known from the prior art.

BRIED DESCRIPTION OF DRAWINGS

Figure 1:
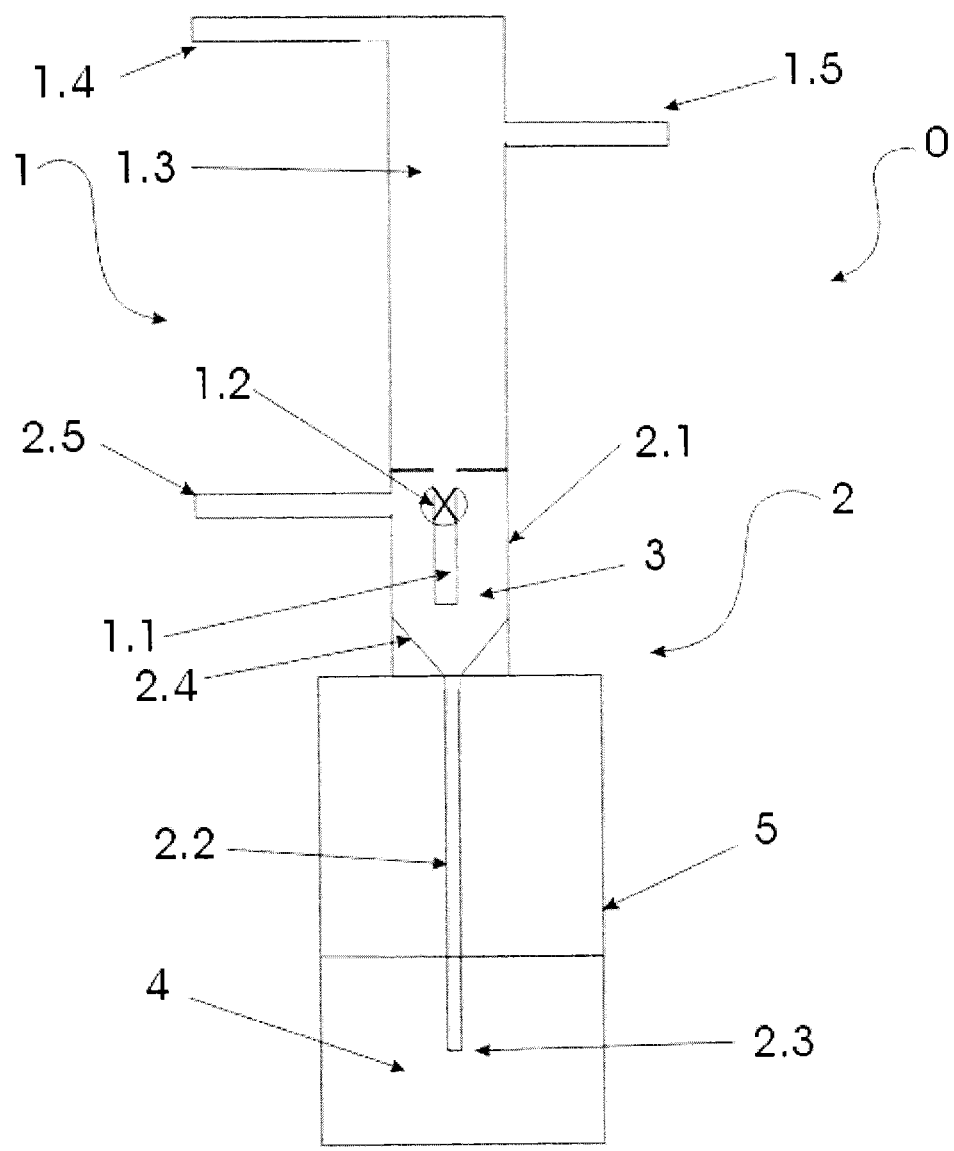

FIG. 1 shows a plant 0 for carrying out the method according to the invention, with a metering device 1 and a control device 1.2.

Figure 2:
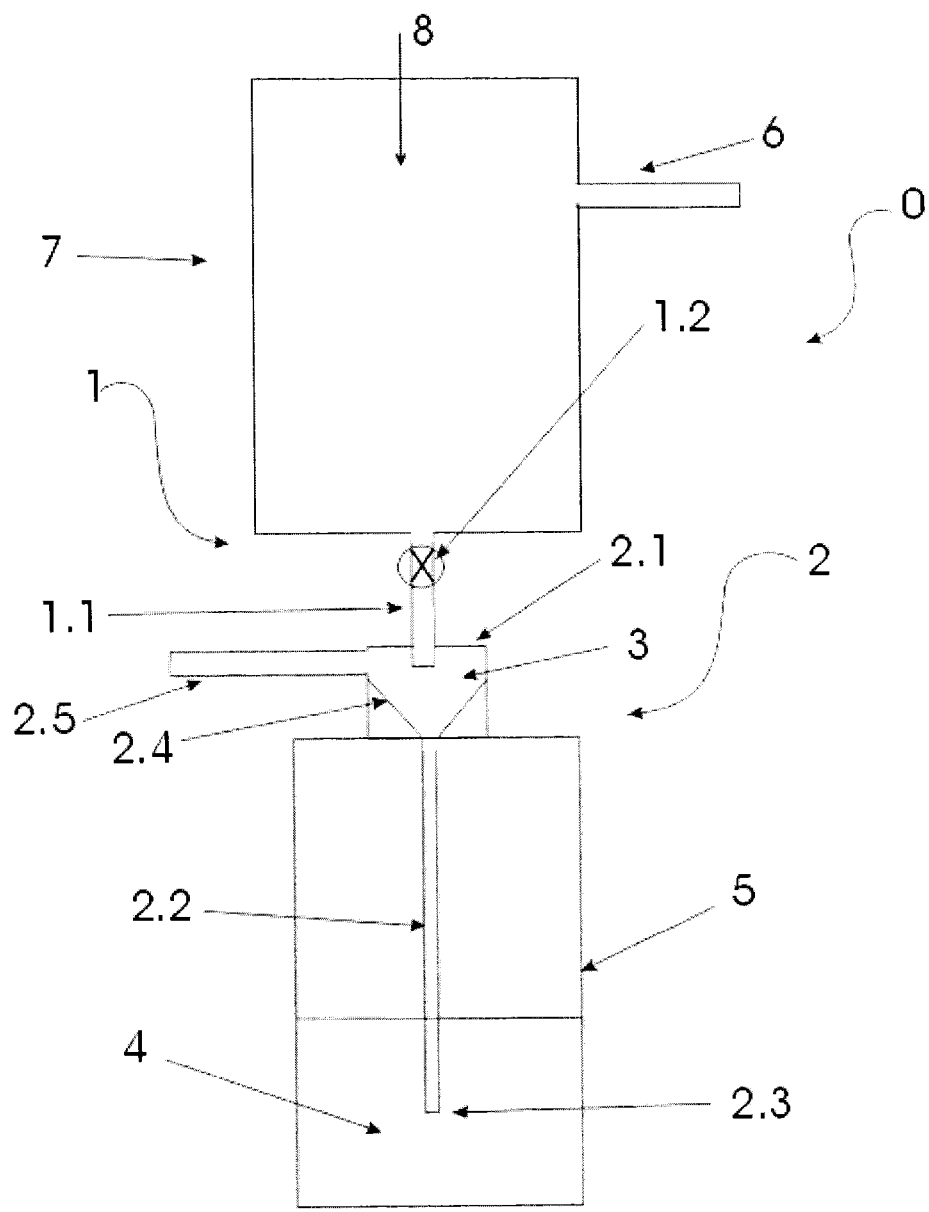

FIG. 2 shows a plant 0 for carrying out the method according to the invention, with a metering device 2 and a control device 1.2.

LIST OF REFERENCE SYMBOLS

0 plant
1 metering device
1.1 feed pipe
1.2 control device
1.3 first vessel
1.4 gas feed pipe
1.5 feed pipe
2 device with delivery means
2.1 second vessel
2.2 delivery means, in particular delivery tube/hose
2.3 end of delivery means
2.4 collecting device
2.5 gas feed pipe
3 lumen
4 solution
5 reactor
6 feed pipe (inert gas)
7 reactor
8 feed pipe (educts)

The problem to be solved by the present invention was to provide a solution containing propyl-functional alkali siliconates and silicates and an economical method of production of propyl-functional alkali siliconate solutions, containing a silicate fraction, and optionally co-condensation products thereof, suitable for hydrophobizing impregnation of mineral building materials, in particular of surfaces of mineral building materials and/or hydrophobizing thereof in the bulk during manufacture. Preferably, porous mineral building materials and/or subsoils are impregnated with the solutions according to the invention. Another problem was to provide stable solutions of the compounds, preferably with a high content of these compounds. Moreover, the solutions should preferably be essentially free from solvents, in particular alcohol free.

The problems were solved by the solution according to the invention and the methods according to the invention, and the solution according to the invention comprising propyl-functional alkali siliconates, alkali silicates and optionally co-condensation products thereof. Further features and combinations thereof are explained in the subclaims and in detail in the description.

The problems are solved by an essentially alcohol-free solution according to the invention containing at least one siliconate and one silicate, wherein it contains, as siliconate, at least one propyl-functional alkali siliconate and optionally its co-condensation products with silicate. Solutions that are especially preferred contain propyl-functional alkali siliconates, at least one alkali silicate and optionally co-condensates thereof. Sodium, potassium and/or lithium may be considered, independently of one another, as alkali, with potassium and sodium being preferred. Especially preferably, solutions according to the invention contain propyl-potassium siliconates, potassium silicates and optionally co-condensation products of propyl-potassium siliconates and potassium silicates. Moreover, it is preferable if the siliconate and silicate are present in the solution in a ratio from 0.5:10 to 10:0.5 or optionally are present in the co-condensate in this ratio, especially preferred ratios are 4:1 to 1:4, 2:1 to 1:2 are further preferred, 1.5:1 to 1:1.5 is further preferred or better still around 1:1. The best results with respect to hydrophobization and dilutability with water can be achieved with these ratios.

A solution preferably means a homogeneous mixture, in particular comprising propyl-functional alkali siliconates, silicates and optionally co-condensation products thereof (together solutes) and at least one solvent, here water, wherein the solutes are preferably dissolved completely in the solvent, here water, i.e. the solution is preferably clear. A solution according to the invention therefore preferably means a homogeneous composition, in which both the propylalkali silicates, the alkali silicates and optionally co-condensation products thereof are dissolved essentially completely. Furthermore, the solution according to the invention is essentially alcohol-free, free from hydrolysis alcohol and preferably free from organic solvents.

According to an alternative for preparation of the solution containing at least one propyl-functional alkali siliconate, a silicate and optionally co-condensation products thereof, a method is claimed in which a propyl-functional alkali siliconate and a silicate are mixed, in particular an aqueous solution of a propyl-functional alkali siliconate, preferably as potassium siliconate, and an aqueous solution of a silicate are mixed, optionally water is added. Moreover, it is preferred if an alkali silicate is used as silicate, especially preferably a sodium silicate and/or a potassium silicate.

According to another alternative of the invention, it was found, surprisingly, that it is possible to prepare solutions of propyl-functional alkali siliconates, silicates and co-condensation products thereof, if preparation takes place from the corresponding silane halogens in the presence of inert gas.

Surprisingly, it was also found that propylsiliconate solutions with a silicate fraction can be prepared by reacting mixtures of propyltrichlorosilanes and tetrachlorosilane in the desired ratio in a step 1 with ethanol or a water/ethanol mixture. The mixture obtained, the reaction product, can be introduced in step 2 into an aqueous lye, preferably an aqueous NaOH or KOH solution. Moreover, it is preferable if the solution is such that after introduction of the mixture the desired final concentration of propyl-siliconate and silicate is obtained. Furthermore, it is preferable if the introduction of the mixture into the solution is carried out in such a way as to ensure that no solid deposits form, in particular of a silicate type. Moreover, the alcohol or a water/alcohol mixture can be used up to 1 to 100 mol. %, in particular 10 to 100 mol. % relative to the hydrolysable residues Si-Hal of compounds I and II, in particular ethanol is used as alcohol. Furthermore, it may be preferable to use a sub-stoichiometric amount of alcohol, such as EtOH or a water/alcohol mixture, such as water/EtOH, in particular 5 to 99 mol. %, preferably 10 to 95 mol. %, especially preferably 20 to 90 mol. %, in particular about 80 mol. %, in each case relative to the molar amount of the hydrolysable Si-Hal bonds or hydrolysable Hal residues on silicon atoms, preferably of general formulae I and II.

Surprisingly it was found that the reaction takes place reliably if the mixture from step 1, the reaction product, is injected by means of a continuous $N_2$ stream into the aqueous lye, i.e. the mixture is distributed immediately in the solution. Moreover, this distribution of the mixture by the combined use of intensive stirring and injection using inert gas is particularly efficient. The formation of solid silicate particles or deposits can be avoided particularly well.

According to the invention, in step 3 the hydrolysis alcohol and added alcohol are removed from the solution obtained and the latter can if necessary be further diluted with water. The alcohol and/or hydrolysis alcohol are preferably removed by distillation, preferably with water being added as alcohol and/or hydrolysis alcohol are removed. Generally, however, even the alcohol-containing solution obtained is already ready for use and is suitable for application. An advantage of the purely aqueous alcohol-free solution is its reduced VOC content in subsequent application.

The three-stage process according to the invention for preparing solutions of propylsiliconates and silicates in aqueous solution comprises a first reaction step, in which a mixture of dipropyldichloro- and/or propyltrichlorosilanes, preferably pure propyltrichlorosilane, and tetrachlorosilane is reacted with a water/ethanol mixture or pure ethanol, and the reaction product obtained is injected, in a second step, by means of an inert gas stream, in particular an $N_2$ gas stream into an aqueous lye, preferably an aqueous alkali hydroxide solution, in a way that prevents the formation of solid deposits, in particular of a silicate type. Moreover, it may be preferable to use a sub-stoichiometric amount of EtOH or water/EtOH mixture, relative to the molar amount of hydrolysable Si-Hal bonds. In the third step the added alcohol and/or hydrolysis alcohol is removed from the solution.

The invention relates to a three-stage method of preparing solutions comprising propyl-functional alkali siliconates, silicates and optionally co-condensation products thereof and optionally a content of alcohol, which are prepared in the presence of an inert gas, alcohol and/or hydrolysis alcohol are removed from the resultant solutions, preferably the alcohol and/or hydrolysis alcohol is removed by distillation under reduced pressure and at elevated temperature. The invention therefore also relates to solutions comprising alkali propylsiliconates, silicates and co-condensation products thereof and solutions obtainable by this method, which are essentially alcohol-free, in particular free from organic solvents.

The invention also relates to a method of preparing a solution comprising at least one propyl-functional alkali siliconate and a silicate and optionally co-condensation products thereof, and essentially alcohol-free solutions obtainable by this method, comprising the steps of:

1) preparing a mixture comprising at least one propyl-functional silane of general formula I, at least one halosilane of formula II and alcohol, in which
   at least one organofunctional silane of general formula I

   $(R^1)_x SiHal_{(y-x)}$ (I)

with $R^1$ independently a propyl residue, such as isopropyl- or n-propyl residue, and with Hal as hydrolysable residue, wherein Hal is independently chlorine or bromine, preferably chlorine, and with x equal to 1 or 2 and with y=4, preferably x=1 and
   at least one halosilane of formula II

   $Si(Hal)_4$ (II)

with Hal as hydrolysable residue, wherein Hal denotes independently chlorine or bromine, preferably Hal denotes chlorine, and
   at least one alcohol and optionally water are reacted, in particular an alcohol-water mixture, in particular the alcohol comprises ethanol, methanol, propanol, such as iso-propanol or n-propanol, or mixtures with at least two of the alcohols, ethanol is preferred;

2) introducing the reacted mixture from step 1 in the presence of inert gas, preferably under inert gas, into an aqueous alkali hydroxide solution, preferably an aqueous NaOH and/or KOH solution; wherein the inert gas is supplied, in the process, in such a way that it introduces the mixture from step 1 a little at a time, preferably dropwise, directly into the aqueous alkaline solution, in particular injects it into the solution or distributes the mixture from step 1 in the solution, especially preferably the mixture from step 1 is distributed homogeneously in the solution.

3) removing the alcohol and/or hydrolysis alcohol, in particular the alcohol is removed by distillation, preferably under reduced pressure and at elevated temperature, wherein it is further preferred that the mixture in step 1 and/or the solution in step 2 are stirred vigorously. Preferably the mixture in step 1 is prepared while stirring vigorously and is also directly incorporated and distributed in the solution in step 2 while stirring vigorously in the presence of an inert gas. Anchor, propeller, cross-jaw, impeller and/or disk stirrers can preferably be used. Furthermore, flow disturbers can be used advantageously. The alcohol used in step 1 is, according to the invention, in the mixture from step 1, also introduced in the second process step into the aqueous alkali hydroxide solution. In contrast to methods of the prior art, separation is not necessary, but can take place optionally after introduction into the aqueous alkali hydroxide solution, e.g. by distillation.

According to the invention, a solution comprising propyl-functional alkali siliconates, silicates and optionally co-condensation products thereof is obtained in step 2, wherein the propyl groups of the siliconate can be independently n-propyl or iso-propyl-. The propyl residue $R^1$ of general formula I is especially preferably n-propyl.

Alkali hydroxide means both alkaline-earth and alkali hydroxides. These are in particular but not exhaustively: lithium hydroxide, sodium hydroxide, potassium hydroxide, magnesium hydroxide, calcium hydroxide, barium hydroxide, which can also be present in mixtures or together with other alkaline, water-soluble salts or compounds. Sodium hydroxide and preferably potassium hydroxide are preferred.

The inert gas can be a gas or carrier gas, with the proviso that it must not react with the educts or products, in particular it must not react with the alkaline solution. Therefore carbon dioxide is not suitable as inert gas. The inert gas preferably comprises nitrogen and/or argon and other gases that do not react with the mixtures and/or solutions. This is for example propane etc. thus, in general, solvents can also be evaporated, such as n-pentane or other vaporizable solvents known by a person skilled in the art. Generally, however, incombustible and ecologically compatible gases are preferred.

Preferred propyl-functional silanes of general formula I are propylhalosilanes, such as an n-propyltrihalosilane, iso-propyltrihalosilane, di-n-propyldihalosilane, di-iso-propyldihalosilane, such as preferably n-propyltrichlorosilane, iso-propyltrichlorosilane, di-n-propyldichlorosilane, iso-propyl-, n-propyldichlorosilane or di-iso-propyldichlorosilane, wherein a person skilled in the art also knows and can use the corresponding brominated or mixed-halogenated propylhalosilanes, in particular comprising chlorine and bromine.

According to the method according to the invention it is preferable if the propyl-functional silane of general formula I and the halosilane of formula II are added, in particular are made available, in step 1 in a molar ratio from 0.5:10 to 10:0.5, preferably in a ratio from 1:10 to 10:1, wherein a ratio of about 1:1 to 9:1 is especially preferred. According to the invention, a ratio of silane of formula I to halosilane of formula II of about 1:1 is used, in particular with a variation of plus/minus 0.5.

Moreover, alternatively or additionally to the aforementioned features, it is preferable if the alcohol; in particular ethanol, methanol, propanol, such as iso-propanol or n-propanol, or mixtures with at least two of the alcohols; is added in step 1 in a ratio from 1 to 100 mol. % relative to the hydrolysable residues, i.e. relative to the total of Hal (halogen atoms in I and II), in particular of chlorine atoms, in mol in general formulae I and II. Thus, if there are approx. 2 mol of chlorine atoms in total in the mixture comprising silanes of formula I and II, then preferably about 0.2 to 2 mol of alcohol, such as preferably ethanol, is added. Preferably 1 to 100 mol. % ethanol relative to the total of chlorine atoms in mol, preferably 5 to 99 mol. %, especially preferably 10 to 95 mol. %, quite especially preferably 20 to 90 mol. %, in particular about 80 mol. %, is added to an alkyltrichlorosilane and tetrachlorosilane, which are present in a ratio from 10:5 to 10:5.

A special feature of the method is that the mixture from step 1 is introduced directly in step 2 into an aqueous, alkaline solution and is converted to a solution comprising propyl-functional siliconates, silicates and optionally co-condensation products thereof, in particular the mixture from step 1 is injected a little at a time, preferably dropwise by means of inert gas directly into the solution or is distributed directly in the solution, i.e. the mixture from step 1 is introduced or injected under the surface of the solution, preferably it is strongly distributed directly. An especially efficient distribution of the solution introduced a little at a time, in particular dropwise, is achieved with a combination of pneumatic distribution, i.e. by the inert gas, and mechanical distribution, such as stirring.

The molar ratio of hydrolysable residues of the mixture from step 1 to the alkali hydroxide used is as a rule between 1:5 to 5:1, preferably it is between 1:3 to 3:1, especially preferably about 1:2 to 2:1, or also about 1:1 with a variation of plus/minus 0.5. Thus, for about 1 mol hydrolysable residues about 2 mol alkali hydroxide can be used or according to an alternative procedure also for about 2 mol hydrolysable groups about 1 mol alkali hydroxide. During addition to the alkali hydroxide solution, the hydrolysable residues comprise the Hal residues and/or the alkoxy groups formed by esterification with the alcohol, in particular on the silanes of general formulae I and/or II as well as optionally on the formed propyl-functional alkali siliconates, silicates and optionally formed co-condensation products thereof.

The alcohol in the solution; in particular ethanol, methanol, propanol, such as iso-propanol or n-propanol, or mixtures with at least two of the alcohols; wherein the solution comprises propyl-functional alkali siliconates, silicates and optionally co-condensation products thereof, is then removed essentially completely. This can preferably take place by distillation. According to the invention, the alcohol is removed by distillation from the solution, to obtain a VOC-reduced solution, which is immediately ready for use and if required can easily be diluted further with water.

In general, the solution, in particular the alcohol-free solution, can be adjusted directly during production to a content of propyl-functional alkali siliconates, alkali silicates and optionally co-condensation products thereof from 1 to 40 wt. % and all values in between—it is immediately ready for use—preferably it can be adjusted to a content from 1 to 30 wt. %, alternatively to 7 to 40 wt. %, especially preferably to 7 to 30 wt. % or also about 8 to 28 wt. %. Using the method according to the invention it is therefore possible to prepare highly concentrated solutions. These highly concentrated solutions are stable, preferably for 12 months. If required the solution can be diluted before use, i.e. a purely aqueous essentially alcohol-free solution, with water and/or with an organic solvent to a content of propyl-functional alkali siliconates, alkali silicates and optionally co-condensation products thereof from 1 to 40 wt. % and to any values in between, preferably to 1 to 30 wt. %, or alternatively to 7 to 40 wt. %, especially preferably to 7 to 30 wt. % or also about 8 to 28 wt. %.

The content is also related directly to the mineral building material used and/or the type of application. Thus, for application on surfaces, solutions with a low content may be suitable, and for example for hydrophobization in the bulk, solutions with a high content, especially for hydrophobization of gypsum-containing mineral building materials. Highly concentrated solutions may also be preferable if water is already added as mixing water for hydrophobization in the bulk. In general the content of active substance can also be between 1 to 10 wt. % in the solution, or depending on the application 1 to 5 wt. %, 5 to 10 wt. %, 10 to 15 wt. %, 15 to 20 wt. % or 20 to 30 wt. % or also 30 to 40 wt. %.

During preparation of the mixture of propyl-functional silane of formula I, the halosilane of formula II and alcohol or alcohol/water mixture, the reaction causes the temperature to rise in step 1. According to the method, the temperature in step 1 should not exceed 80° C., especially preferably the temperature should not exceed 60° C., and cooling is used if necessary. Reaction also causes the temperature to rise in step 2, but it should not exceed 80° C., preferably should not exceed 60° C., i.e. cooling is used if necessary in step 2 or the mixture from step 1 is introduced more slowly, a little at a time into the alkaline solution. In step 3 preferably the alcohol and/or hydrolysis alcohol are preferably removed under vacuum, in such a way that the temperature does not rise above 80° C., preferably not above 60° C. Therefore the alcohol and/or hydrolysis alcohol are removed from the solution preferably by distillation at 300 mbar, preferably at 180 mbar. The solution temperature can be controlled to about 50° C.

On introduction of the mixture from step 1 into the alkali hydroxide solution there can be formation of propyl-functional alkali siliconates, such as $MO[Si(R^1)_xY_{(y-2)-x}O]_aM$ of the idealized formula III or $MO[Si(R^1)_xO^-_{(y-2)-x}O]_aM+M_a$ of the idealized formula IIIa, alkali silicates, such as $MO[Si(Y)_2]_bOM$ of the idealized formula IV, and optionally co-condensation products thereof, in particular organofunctional co-condensates of alkali siliconates and alkali silicates, which are preferably in the form of propyl-functional alkali siloxanolates and which comprise alkali silicates, for example according to formula V shown in idealized form $MO[Si(R^1)_xY_{(y-2)-x}O]_a[Si(Y)_2]_bOM$ or formula Va shown in idealized form $MO[Si(R^1)_xY_{(y-2)-x}O]_a[Si(Y)_2]_b[Si(R^1)_xY_{(y-2)-x}O]_aOM$, where Y in formulae III, IIIa, IV, V and/or Va in each case independently $Y=O_{1/2}$ in a siloxane bond or OM, with M denoting a monovalent alkali ion, such as Na$^+$ or K$^+$; or ½ alkaline-earth ion, such as $½Ca^{2+}$, in —ONa, —OK, or hydrogen for —OH, R$^1$ as defined, with a and b independently of one another greater than or equal to 1 and in each case independently x=1 or 2 and y=4, preferably x=1. Preferably a and b can be greater than or equal to 2, for example between 2 and 30. Moreover, both the propyl-functional alkali siliconates, the alkali silicates and optionally the co-condensation products can have both linear, cyclic, branched and/or three-dimensional network structures, as they are derived from bi-, tri- and tetrafunctional hydrolysable silanes.

The invention also relates to a method in which the mixture from step 1 is supplied, for the execution of step 2, by means of a metering device, which in the simplest case has a control device, such as a shut-off device or a shut-off valve, optionally in the presence of inert gas, in particular an inert gas under pressure, preferably above from 1 bar to 10 bar, a little at a time, in particular dropwise, to a device with a delivery means, wherein the delivery means is preferably a delivery tube or hose, and the device is shielded with inert gas, in particular in the lumen with inert gas, and the end of the delivery means, in particular of the delivery tube or hose, is immersed in the alkaline solution, or, that the mixture from step 1 is transferred, for the execution of step 2, to a metering device and is shielded with inert gas, in particular with an inert gas under pressure, preferably with a pressure from 1 bar to 10 bar, the mixture from step 1 is transferred from the metering device a little at a time, in particular dropwise, to a device with a delivery means, in particular the delivery means is a delivery tube or hose, wherein the device is shielded with inert gas, and the end of the delivery means, in particular of the delivery tube or hose, is immersed in the alkaline solution. It may also be desirable if the end of the delivery means is immersed just under the surface, especially preferably it is immersed in the solution as deeply as possible.

Moreover, it is further preferred if the method is carried out in such a way that an inert gas stream, for example a nitrogen and/or argon stream, is divided and one portion of the inert gas is transferred to the metering device, in particular via the gas feed pipe, and one portion of the inert gas is transferred to the device with delivery means, in particular via the gas feed pipe. Preferably the delivery means is a delivery tube and/or hose. Preferably the inert gas stream on the two aforementioned gas feed pipes is coupled, to make the metering and process control economical.

Additionally or alternatively to one or more of the aforementioned features, it is further preferable if the mixture from step 1 is transferred by means of the metering device a little at a time to the device with the delivery means, i.e. preferably to the delivery tube, and there it is forced by the inert gas through the delivery means, in particular delivery tube, into the alkaline solution, preferably the mixture from step 1 is in each case forced dropwise directly into the solution, especially preferably the mixture from step 1 is injected by the inert gas directly into the solution, more preferably the mixture from step 1 is injected by the inert gas under pressure into the solution. Moreover, the drops are preferably in each case separated from one another by the inert gas. Additionally, the distribution and dilution of mixture 1 from step 1 at the end of the delivery means in the aqueous alkali hydroxide solution can be further supported by vigorous stirring.

In the method according to the invention, in step 3 the alcohol and/or hydrolysis alcohol is removed, in particular the alcohol is removed by distillation, preferably under reduced pressure and at elevated temperature. Distillation is preferably carried out at below 300 mbar, more preferably below 180 mbar and in particular at about 50° C.

The invention also relates to a solution obtainable by the method according to the invention, which is essentially alcohol-free and/or which preferably has co-condensation products of propyl-functional alkali siliconates with silicates, in particular alkali silicates, more preferably potassium silicate. A solution is regarded as essentially alcohol-free and/or free from hydrolysis alcohol if it has a content of preferably less than 1 ppm by weight up to maximum 2 wt. % of alcohol and/or hydrolysis alcohol, preferably between 10 ppm by weight and 1 wt. %, especially preferably between 100 ppm by weight and 0.5 wt. %, in each case relative to the total weight of the solution. The essentially alcohol-free solution has a flash point of above 100° C.

The invention further relates to the use of a solution according to the invention or a solution that has been prepared by the method according to the invention for the hydrophobization of mineral building materials, in particular a solution that is essentially alcohol-free, preferably for the hydrophobization of the surface of mineral building materials or for the hydrophobization of mineral building materials in the bulk. Moreover, the use of the solution can be used for the hydrophobization of a portion of the mineral building material or also for the hydrophobization of the whole mineral building material, in each case comprising concrete, screed, plaster, gypsum, mortar, loam, clay, sand, ceramic, terracotta, lime sandstone, natural stone, such as sandstone, marble, granite and articles therefrom or articles containing them, such as moulded articles, comprising for example pipes, bricks, floor tiles, walls, garden tubs, roof tiles and other usual mineral building materials and articles made from these building materials, known by a person skilled in the art.

The following examples explain the method according to the invention and the equipment according to the invention in more detail, without limiting the invention to these examples.

EXAMPLES

Examples of a Plant for Carrying Out the Method

FIG. 1 shows a plant 0 for carrying out the method according to the invention, with a metering device 1 and a control device 1.2, which permits the metering of the mixture from step 1 a little at a time into the delivery means 2.2. The metering device 1 can also comprise a) a first vessel 1.3 with a gas feed pipe 1.4 and/or a feed pipe (1.5, as shown in FIG. 1 or b) the plant comprises a metering device 2 (FIG. 2) with control device 1.2 and comprises a step 1 reactor (7) with a feed pipe for educts 8 and optionally a feed pipe for inert gas 6. The metering device 1 is connected to a device 2, which has a delivery means 2.2, which can usually be a delivery tube 2.2 or a delivery hose 2.2. In addition, the device 2 has a so-called second vessel 2.1, whose purpose, which is a kind of mixing chamber of inert gas and portions or drops of the mixture from step 1. For this, the second vessel 2.1 has a lumen 3 and a gas feed pipe 2.5 and is connected to the delivery means 2.2, in particular delivery tube or hose 2.2, wherein the end 2.3 of the delivery means is led into a step 2 reactor (5). Moreover, the length of the delivery means is such that the end 2.3 is immersed in the solution 4. Preferably the end is immersed in the solution 4 as deeply as possible.

In FIGS. 1 and 2 it is shown schematically that a plant 0 is to be suitable for transferring the mixture from step 1 with a control device 1.2, which is optionally connected to the first vessel 1.3 or the step 1 reactor (7), preferably by means of a feed pipe 1.1, defined in the lumen 3 of the second vessel 2.1. There, the mixture from step 1 is shielded with inert gas and the individual drops are virtually separated by the inert gas. It is therefore important that the delivery means preferably has a diameter or is such that a coalescence of the portions or drops in the delivery means itself is prevented in continuous metering. In addition, a gas feed pipe 2.5 is connected to the vessel 2.1. The vessel 2.1 can have a kind of collecting device 2.4 for example of the nature of a funnel, which is located above the delivery means 2.2. The delivery means is preferably a rigid tube or a capillary 2.2, the bottom end of which 2.3 is introduced into the reactor 5 so far that the end 2.3 is immersed in the solution 4 during execution of the method. Moreover, the second vessel 2.1 can have a lumen 3, which makes it possible to introduce the mixture from step 1 for example dropwise in the presence of nitrogen into the delivery tube separately and inject it directly into the solution in the reactor of step 2. It can therefore be sufficient if the second vessel 2.1 represents a kind of expansion in the delivery means 2.2 with gas feed pipe 2.5.

Example 1

Preparation of an 8% Aqueous Solution of K-Propylsiliconate and K-Silicate:

100 g of a 1:1 mixture (based on the molar composition) of propyltrichlorosilane and tetrachlorosilane was put in a 250-ml round-bottomed flask with dropping funnel and gas offtake tube. 10 g ethanol was added slowly, stirring vigorously. The temperature rose during addition, but was not to exceed 60° C. It was cooled down if necessary. After all of the ethanol had been added, it was stirred for a further 10 min and the mixture obtained was used further directly. 300 g of 40% aqueous KOH was put in a 500 ml round-bottomed flask (5) with gas delivery tube (2.2) without frit. 50 g of the product from the first reaction step was put in a dropping funnel (1) with $N_2$ connection (1.4). The product was now added slowly, stirring vigorously, via the gas delivery tube (2.2) to the aqueous lye (4). The $N_2$-stream is divided so that one portion exerts pressure on the contents of the dropping funnel (1), and the other portion flows round the opening of the dropping funnel (1.1 in 3 of device 2). The two streams are combined again in the gas delivery tube (2.2). During addition, the temperature rose. Were it to rise above 60° C., it was to be cooled down. After complete addition, stirring was continued until a clear solution was obtained.

$^{29}$Si-NMR (100 MHz, $D_2O$): δ=−46 ($CH_3CH_2CH_2Si$ ($O^-$)$_3$), −71 ($Si(O^-)_4$).

Then, at 180 mbar and a bath temperature of 50° C., the ethanol was distilled off and an amount of water corresponding to the amount of ethanol distilled off was added.

Example 2

Preparation of an 11% Aqueous Solution of K-Propylsiliconate and K-Silicate:

100 g of a 1:1 mixture (based on the molar composition) of propyltrichlorosilane and tetrachlorosilane was put in a 250 ml round-bottomed flask with dropping funnel and gas offtake tube. 10 g ethanol was added slowly, stirring vigorously. The temperature rose during addition, but was not to exceed 60° C. It was cooled down if necessary. After all of the ethanol had been added, it was stirred for a further 10 min and the mixture obtained was used further directly. 440 g of 50% aqueous KOH was put in a 500 ml round-bottomed flask (5) with gas delivery tube (2.2) without frit. 100 g of the product from the first reaction step was put in a dropping funnel (1) with $N_2$ connection (1.4). The product was now added slowly, stirring vigorously, via the gas delivery tube (1.4) to the aqueous lye (4). The $N_2$-stream was divided so that one portion (1.4) exerts pressure on the contents of the dropping funnel (1), and the other portion (2.5) flows round the opening of the dropping funnel (1.1 in 3 of device 2). The two streams were combined again in the gas delivery tube (2.2). During addition, the temperature rose. If it was over 60° C., it was cooled down. After complete addition, stirring was continued until a clear solution was obtained.

$^{29}$Si-NMR (100 MHz, $D_2O$): δ=−45.6 ($CH_3CH_2CH_2Si$ ($O^-$)$_3$), −70.5 ($Si(O^-)_4$).

Then the ethanol was distilled off at 180 mbar and a bath temperature of 50° C. and an amount of water corresponding to the ethanol distilled off was added.

Example 3

(Mixture According to the Invention, Approx. 479 Ppm Active Substance):

1:1 mixture of n-propylsiliconate and silicate: 200 ml of demineralized water was added to 320 mg of an approx. 30% aqueous solution of a 1:1 mixture of potassium propylsiliconate and potassium orthosilicate and the mixture was stirred for 15 min at room temperature. The resultant solution was used directly.

4. Comparative Example

Example for WO 02/083808, Approx. 560 Ppm Active Substance

1:1 mixture of methylsiliconate and silicate: 200 ml of demineralized water was added to 160 mg of an approx. 34% aqueous solution of potassium methylsiliconate and 160 mg of soda waterglass (35.5% in water, obtainable from the company Carl Roth GmbH) and the mixture was stirred for 15 min at room temperature. The resultant solution was used directly.

5. Comparative Example

Example for WO 02/083808, Approx. 490 Ppm Active Substance

1:1 mixture of methylsiliconate and silicate: 200 ml of demineralized water was added to 120 mg of an approx. 34% aqueous solution of potassium methylsiliconate and 160 mg soda waterglass (35.5% in water, obtainable from the company Carl Roth GmbH) and the mixture was stirred for 15 min at room temperature. The resultant solution was used directly.

Tests:

Massive brick cubes from Poroton solid brick with an edge length of 50 mm were conditioned at 25° C. and 60% humidity for 24 h and then immersed for 5 s in the solutions from examples 3, 4 and 5. Adhering moisture was removed by lightly dabbing the surfaces with a paper cloth. The amount of product absorbed was determined by weighing.

Then the treated test specimens were stored at 25° C. and 60% humidity for 14 days, in such a way that air could reach all sides. The reduction of water absorption was determined on these specimens on the basis of DIN EN 13580. The percentage reduction was calculated by comparing with an untreated specimen of the same type (Table 1). The following Table 1 shows amounts used and reduction of water absorption before and after storage in KOH.

TABLE 1

Reduction in water absorption of brick Examples 3, 4 and 5
Storage in KOH, 24 h on the analogy of DIN EN 13580.

| Example | Amount of product absorbed [g/m$^2$] | Reduction in water absorption [%] | Reduction in water absorption [%] after storage in KOH |
|---|---|---|---|
| 3 | 353.3 | 12.2 | 12.5 |
| 4 | 366.7 | 9.0 | 9.9 |
| 5 | 380 | 4.2 | 4.9 |

The results in Table 1 clearly show that with a comparable amount as well as with a smaller amount of product absorbed and with comparable concentrations of active substance, a definite improvement in reduction of water absorption is possible, using the mixture according to the invention from example 3.

6. Comparative Example

Preparation of an 8% Aqueous Solution of K-Propylsiliconate and K-Silicate 100 g of a 1:1 mixture (based on the molar composition) of propyltrichlorosilane and tetrachlorosilane was put in a 250 ml round-bottomed flask with dropping funnel and gas offtake tube. 10 g ethanol was added slowly, stirring vigorously. The temperature rose during addition. However, it was not to exceed 60° C. It was cooled down if necessary. After all of the ethanol had been added, it was stirred for a further 10 min and the mixture obtained was used further directly.

300 g of 40% aqueous KOH was put in a 500 ml round-bottomed flask with gas delivery tube without frit. 50 g of the product from the first reaction step was put in a dropping funnel without N$_2$ connection. The product was now added slowly, stirring vigorously, via the gas delivery tube to the aqueous lye. Addition had to be stopped after just a few millilitres, as the feed lines became clogged.

The invention claimed is:

1. A method of preparing an alcohol-free solution comprising a propyl-functional alkali siliconate, a silicate and optionally a co-condensation product of a propyl-functional alkali siliconate with a silicate, the method comprising:
   1) preparing a mixture comprising a propyl-functional silane, a halosilane, and an alcohol by reacting the propyl-functional silane, halosilane, alcohol, and optionally water
   2) introducing the mixture in the presence of inert gas into an aqueous alkaline hydroxide solution, wherein the inert gas is supplied so that the mixture is metered directly into the aqueous alkaline hydroxide solution, and
   3) removing alcohol and/or hydrolysis alcohol,
   wherein the propyl-functional silane is represented by the formula I:

$(R^1)_x SiHal_{(y-x)}$ (I), wherein $R^1$ is independently a propyl-functional residue; hydrolysable residue Hal is independently chlorine or bromine;
   x is 1 or 2; and
   y is 4, and
   the halosilane is represented by the formula II:

$Si(Hal)_4$ (II), wherein hydrolysable residue Hal is independently chlorine or bromine.

2. The method according to claim 1, further comprising: stirring the mixture during the preparing vigorously.

3. The method according to claim 1, further comprising: obtaining a solution comprising a propyl-functional alkali siliconate, a silicate and optionally a co-condensation product of a propyl-functional alkali siliconate with a silicate during the introducing.

4. The method according to claim 1, further comprising: mixing the propyl-functional silane and the halosilane in a molar ratio from 0.5:10 to 10:0.5.

5. The method according to claim 1, further comprising: adding the alcohol in a ratio from 1 to 100 mol.% relative to the hydrolysable residue in mol.

6. The method according to claim 1, further comprising: introducing the mixture into an aqueous alkaline solution immediately after the preparing to be reacted to a solution comprising a propyl-functional siliconate, a silicate and optionally an co-condensation product of a propyl-functional siliconate with a silicate.

7. The method according to claim 1, wherein the removing is carried out by distillation.

8. The method according to claim 1, wherein the proportion of the propyl-functional siliconate, silicate and co-condensation product of the propyl-functional siliconate with the silicate in the alcohol-free solution is from 1 to 40wt. %, relative to a total weight of the alcohol-free solution,
   wherein amounts of the propyl-functional siliconate, silicate and co-condensation product of the propyl-functional siliconate with the silicate may be adjusted by adding water.

9. The method according to claim 1, comprising: transferring the mixture with a metering device into a device with a delivery means and forcing with the inert gas through the delivery means into an alkaline solution.

10. The method according to claim 1, further comprising: stirring the aqueous alkaline hydroxide solution during the introducing vigorously.

* * * * *